United States Patent
Hertz

[11] Patent Number: 5,839,946
[45] Date of Patent: Nov. 24, 1998

[54] HANDHELD APPARATUS FOR PROPELLING PARTICULATE MATTER AGAINST A SURFACE OF A PATIENT'S TOOTH, AND METHOD

[76] Inventor: Reuben Hertz, 2717 E. Oakland Park Blvd., Ft. Lauderdale, Fla. 33306

[21] Appl. No.: 517,379

[22] Filed: Aug. 21, 1995

[51] Int. Cl.$^6$ .................................................. B24C 7/00
[52] U.S. Cl. ............................................. 451/90; 451/99
[58] Field of Search ............................. 451/102, 90, 38, 451/99

[56] References Cited

U.S. PATENT DOCUMENTS

| | | | |
|---|---|---|---|
| 2,133,149 | 10/1938 | Poncelet | 51/8 |
| 2,441,441 | 5/1948 | Paasche | 451/90 |
| 2,577,465 | 12/1951 | Jones et al. | 51/8 |
| 2,641,087 | 6/1953 | Greiser | 51/12 |
| 2,696,669 | 12/1954 | Ikse | 32/28 |
| 2,725,684 | 12/1955 | Crowe | 451/90 |
| 2,744,361 | 5/1956 | Larson et al. | 51/11 |
| 3,164,153 | 1/1965 | Zorzi | 128/224 |
| 3,631,631 | 1/1972 | Greenstein | 451/90 |
| 4,369,607 | 1/1983 | Bruggeman et al. | 51/427 |
| 4,475,370 | 10/1984 | Stark et al. | 451/89 |
| 4,941,298 | 7/1990 | Fernwood et al. | 451/99 |

*Primary Examiner*—Robert A. Rose
*Attorney, Agent, or Firm*—Gerald E. Linden

[57] ABSTRACT

A disposable apparatus for propelling particulate matter against a surface of a target material includes, a mixing chamber having a chamber wall and a gas receiving port in the chamber wall in fluid communication with the compressed gas source and having a mixture discharge port in the chamber wall, a gas delivery conduit extending from the gas receiving port into the chamber, a mixture discharge conduit extending from the mixture discharge port into the chamber, and a quantity of particulate matter inside the chamber. A method is provided for propelling particulate matter against a surface of a target material using the above-described apparatus, including the steps of delivering a stream of gas into the air delivery conduit and into the mixing chamber from the gas source, so that the gas stream blows through the quantity of particulate matter, causing the particulate matter to mix with the gas stream, forming a gas and particle mixture, and discharging the mixture through the discharge conduit and the discharge port to strike the surface of the target material.

30 Claims, 4 Drawing Sheets

HANDHELD APPARATUS FOR PROPELLING PARTICULATE MATTER AGAINST A SURFACE OF A PATIENT'S TOOTH, AND METHOD

BACKGROUND OF THE INVENTION

1. Field of the Invention

The present invention relates generally to the field of devices for propelling particulate matter against a surface of target material to sand blast, abrade, etch, erase, cut, smooth, clean, polish and harden the surface. More specifically, the present invention relates to a totally disposable, inexpensive particle propelling apparatus powered by a compressed gas source, including a cylindrical chamber having a chamber wall and a gas receiving port in the chamber wall in fluid communication with the compressed gas source, a gas delivery conduit extending from the gas receiving port into the chamber, a mixture discharge port in the chamber wall, a mixture discharge conduit extending from the mixture discharge port into the chamber, a particle directing hollow tube in fluid communication with the discharge port, and a measured quantity of a specific particulate matter sealed inside the chamber. The apparatus is preferably made of inexpensive plastic and metal, so that the entire unit and contents are cleanly manufactured and sealed and, if necessary, can be sterilized at the place of manufacture, and the entire apparatus is economically replaced rather than re-used.

A method of apparatus use is also provided. Pressurized gas is delivered through the gas receiving port, the gas delivery conduit and into the chamber from the gas source. The velocity of the gas stream progressively blows through the particulate matter and causes the particulate matter to cyclically spin in the chamber, mixing with the gas stream. The gas and particle mixture passes and accelerates through the discharge conduit, the discharge port, and the directing tube, and exits the apparatus to strike the target material surface.

2. Description of the Prior Art

There have long been devices and methods for impacting surfaces of a target material with specific particulate matter. This may be done for a variety of reasons, such as to remove foreign material, roughen or etch the surface to enhance bonding quality, or to dull an unsightly shine. As the gas and particulate matter bombard the target material at high speed, the impact of the particles causes layers of the target material to sheer one at a time. This process of material removal is known as etching and also as sand-blasting.

Devices of many sizes and types are available for this process, and they are powered by many types of compressed gases such as air, nitrogen, oxygen, and others. Large devices have been provided for cutting through metals and smoothing surfaces of casting parts, while small ones have been designed for the art industry and dentistry. All of these devices operate on the physical property that gas at higher pressure flows and accelerates toward and into gas at lower pressure. When particulate matter is mixed with gas at higher pressure, it is accelerated with the gas.

This technique utilizes kinetic energy (Ek) from particles entrained in a high-velocity stream of gas to remove material structure. The term kinetic energy was coined by Lord Kelvin and is defined mathematically by the equation Ek equals one half the mass times the square of the velocity.

While many devices operating on this principle have been designed specifically for the art industry, construction, general industry, dental, and veterinary services, none may be considered disposable, since their cost is many times more than the profit derived from a single procedure. As a result, these devices are designed for long term use and repeated cleaning and maintenance cycles. For example, the devices are designed to be refilled with particulate matter and to operate at high pressures. These functional characteristics require that existing devices have larger overall sizes and bulky nozzles made of expensive carbide alloys. Since these devices are not disposable, individuals must be skilled to maintain, clean, refill and re-assemble them. This presents an opportunity for unit malfunction for contamination of the material and of the user, and for loading with inappropriate and even dangerous particulate material by mistake.

Examples of these prior devices include that described in Fernwood, U.S. Pat. No. 4,941,298, issued on Jul. 17, 1990. Fernwood discloses a rear reservoir micro sandblaster which includes a hollow tubular handle with a nozzle at one end for dispensing a mixture of a solid material and a gaseous medium, and a compressed air and solid particulate material receiving member at the other end of the handle. The nozzle section of the apparatus contains a mixing chamber where a vacuum is created by the flowing pressurized gaseous medium, drawing solid material into the chamber from a rear reservoir. Problems with Fernwood are that it is too costly to be disposable; it draws particulate matter from a container using a vacuum rather than by more efficient blow through mixing of as per our invention, and is thus sensitive to variations in material and gas moisture levels, and requires an unclogging mechanism. Fernwood operates at relatively high pressures, 80–100 psi, requiring a special tap into the air lines and limiting the range of operational pressures. In addition, Fernwood requires special training to set up and use, cannot be cost effectively and completely sterilized between use, cannot deliver varying sizes of particles, and is contaminated after every use.

The apparatus disclosed in the Microetcher™ brochure is either the same or very similar to that of Fernwood. Another similar device, with a forward material reservoir, is disclosed in the Mirage/Chameleon Dental Products, Inc. brochure and is called the Handiblaster™. Other similar devices are the Microetcher II™ disclosed in brochure headed: "Now With Autoclavable Tip" and the AEC Air Eraser™ revealed in Paasche™ operating instructions.

It is thus an object of the present invention to provide a sandblasting apparatus which delivers a mixture gas and particulate matter against a surface of target material.

It is another object of the present invention to provide such an apparatus which is provided pre-loaded from the factory with a select quantity of specific particulate matter and which is sealed.

It is another object of the present invention to provide such an apparatus which accelerates and directs particulate matter through the barrel of a hollow tube, which can be bent to become omni-directional, which is long enough to deliver the matter at a substantially uniform velocity, and which is narrow enough to focus discharged matter over a small target in a confined area.

It is another object of the present invention to provide such an apparatus which is marked with a grid to measure the quantity of particulate matter discharged and which is color-coded to identify the contents inside the given apparatus.

It is another object of the present invention to provide such an apparatus which has a mixing chamber narrow enough to be handled in the manner of a writing instrument such as a pen, which is balanced and operational at all orientations and external pressures, and is totally sterilizable and disposable.

It is still another object of the present invention to provide such an apparatus and method which creates a turbulent mixture of gas and particulate matter via blow through mixing of the gas stream on the particulate matter.

It is finally an object of the present invention to provide such an apparatus which is sufficiently inexpensive to manufacture to be disposable and to manufacture cleanly so that contamination is not compromised during filling, and which is totally recyclable.

SUMMARY OF THE INVENTION

The present invention accomplishes the above-stated objectives, as well as others, as may be determined by a fair reading and interpretation of the entire specification.

A disposable apparatus powered by compressed gas is provided for propelling particulate matter against a surface of a target material, including a mixing chamber having a chamber wall and a gas receiving port in the chamber wall in fluid communication with a compressed gas source and having a mixture discharge port in the chamber wall, a gas delivery conduit extending from the gas receiving port into the chamber, a mixture discharge conduit extending from the mixture discharge port into the chamber, and a quantity of particulate matter inside the chamber, where a stream of gas having a pressure is delivered into the gas delivery conduit and into the mixing chamber from the gas source, the velocity of the gas stream progressively blows through the quantity of particulate matter and causes the particulate matter to mix with the gas stream, forming a gas and particle mixture which enters and passes through the discharge conduit and the discharge port, and exits the apparatus to strike the surface of the target material. The mixing chamber wall preferably has a tubular side wall portion and two opposing end wall portions. The apparatus preferably additionally includes a hollow particulate matter directing tube. The chamber is optionally formed of a translucent plastic, and is optionally color-coded to identify the particulate matter contained within the chamber.

An apparatus is also provided for propelling particulate matter against a surface of a target material, including a mixing chamber having a chamber wall and a gas receiving port in the chamber wall and having a mixture discharge port in the chamber wall, a gas delivery conduit extending from the gas receiving port into the chamber, a mixture discharge conduit extending from the mixture discharge port into the chamber, and a quantity of particulate matter inside the chamber.

A method is provided of propelling particulate matter against a surface of a target material using the above-described apparatus, including the steps of delivering a stream of gas into the gas delivery conduit and into the mixing chamber from the gas source, so that the flow of the gas stream progressively blows through the quantity of particulate matter, causing the particulate matter to mix with the gas stream, forming a gas and particle mixture, and discharging the mixture through the discharge conduit and the discharge port to strike the surface of the target material.

BRIEF DESCRIPTION OF THE DRAWINGS

Various other objects, advantages, and features of the invention will become apparent to those skilled in the art from the following discussion taken in conjunction with the following drawings, in which.

DETAILED DESCRIPTION OF THE PREFERRED EMBODIMENTS

Figures 1, 2:
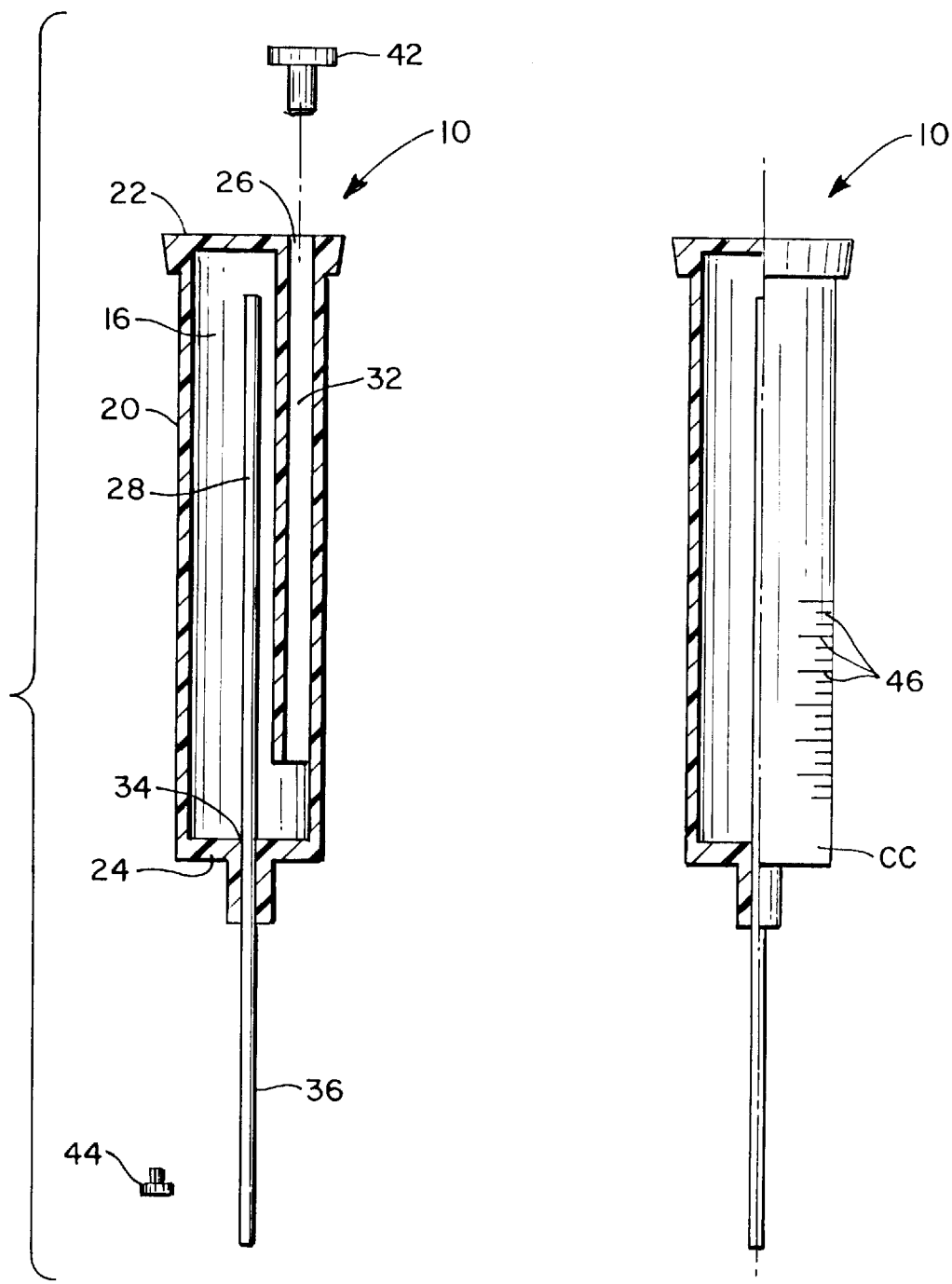
FIG. 1 is a cross-sectional side view of the preferred embodiment of the inventive particle-propelling apparatus. The particulate matter and gas source are omitted.
FIG. 2 is a partial cross-sectional side view of the apparatus of FIG. 1, revealing some of the outer chamber side wall having the optional grid measuring markings and a circumferential color-code band.
Figure 3:
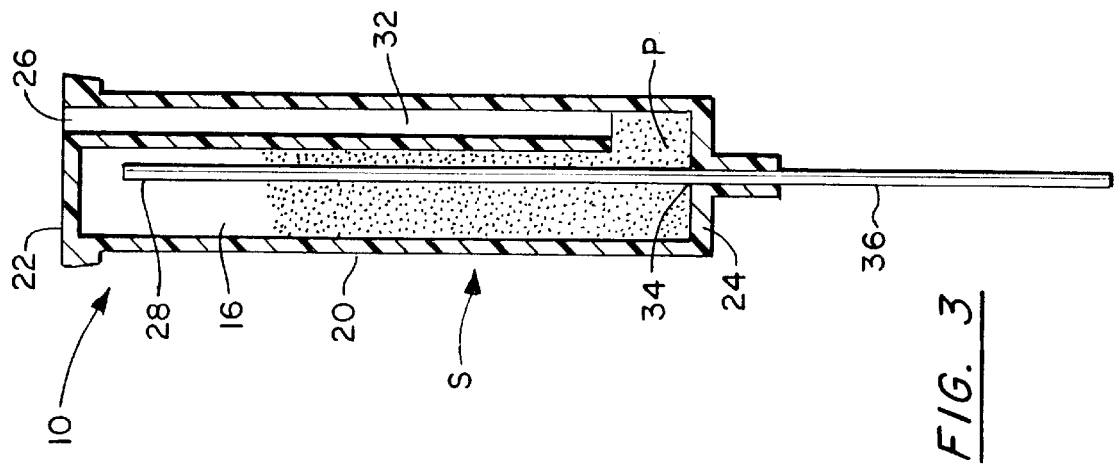
FIG. 3 is a view as in FIG. 1, showing the apparatus with the particulate matter added.
Figure 2A:
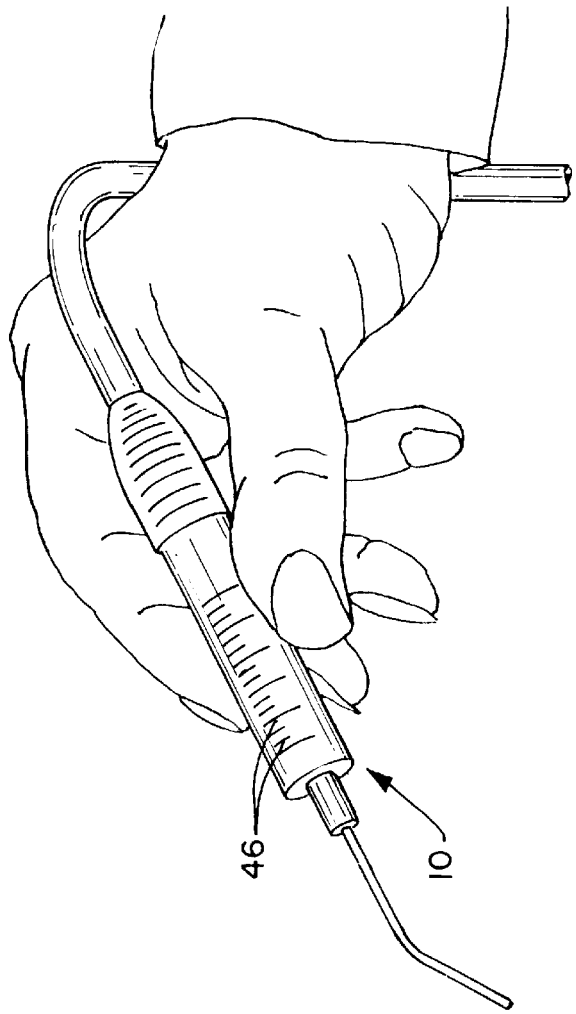
FIG. 2a is a perspective view of the apparatus of FIG. 2 in the hand of a user ready for operation.
Figure 4:
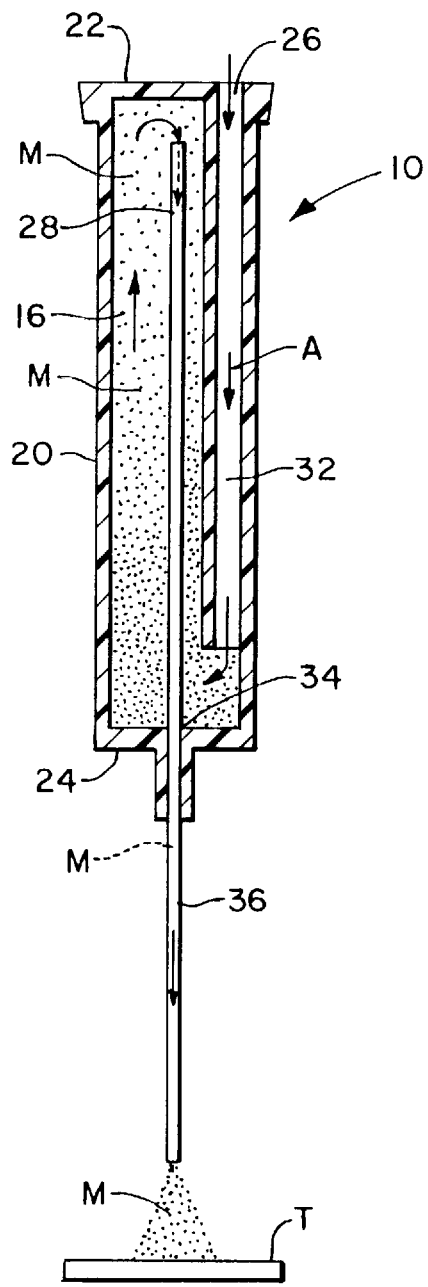
FIG. 4 is a view as in FIG. 3, with the apparatus in operation, discharging the gas and particulate matter mixture toward a surface of a target material.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURES are designated by the same reference numerals.

First Preferred Embodiment

Referring to FIGS. 1–4, a disposable particle propelling apparatus 10 is disclosed for propelling particulate matter P against target material T. The apparatus 10 includes a cylindrical mixing chamber 16 having a chamber wall 20 and two end wall portions 22 and 24, respectively. Apparatus 10 is powered by a compressed gas source such as an air compressor or a compressed gas cylinder (not shown), which connects in fluid communication to the gas receiving port 26 of end wall portion 22. The gas delivery conduit 32 extends from the gas receiving port 26 into mixing chamber 16. End wall 24 has a mixture discharge port 34. A mixture discharge conduit 28 extends. in fluid communication from mixture discharge port 34 into mixing chamber 16. A particle directing tube 36 is provided in fluid communication with discharge port 34 and extends opposite discharge conduit 28 outside from mixing chamber 16.

A quantity of particulate matter P is sealed inside chamber 16, the quantity being sufficient to only partially fill chamber 16, leaving space for gas and particulate matter P to mix. The complete sealing of the particulate matter P gives matter P a virtually unlimited shelf life and protection from contamination. Mixing chamber 16 provides a gas-tight seal to maintain particle sterility and to prevent gas leakage during operation. An inlet cap 42 and a tip cap 44 seal gas receiving port 26 and mixture discharge port 34, respectively, and are removed when apparatus 10 is to be connected to the compressed gas source for use. Volume grid markings 46 are preferably provided on the wall side portion 20 of chamber 16 so that the quantity of particulate matter P used can be measured and visually observed when wall 20 is constructed of a clear of opaque material. Chamber wall 20 may also be color-coded to identify the type of particulate matter P. The color code marking CC may indicate the particle size and the type of particulate matter P.

Tube 36 serves to both direct and accelerate the discharging gas and particulate matter P mixture. As result, the particulate matter P can be applied to a focused region very precisely and at a uniform velocity. Since apparatus 10 is disposable, tube 36 can be inexpensively thin walled to sustain a limited use. Tube 36 is manually bendable permitting it to be quickly set to any angle, making the discharge omni-directional, to provide access to-hard-to reach surfaces. Tube 36 preferably has a preset orifice diameter to accommodate a given size and type of particulate matter P, and is preferably made of metal, but may also be formed of suitable plastic or other material.

Chamber 16 is preferably an integrated chamber with balanced distribution of weight which is preferably slender enough to hold and manipulate as though it were a writing instrument. The direct, blow through, turbulent mixing within chamber 16 makes apparatus 10 operational at all orientations relative to the target surface and to the direction of gravity. The slender construction makes chamber 16 able to access narrow spaces and operate in small confined areas. Chamber 16 can receive and function with varying gas pressures applied to gas receiving port 26, selected to accelerate particles to various desired velocities for various given tasks. Turbulent mixing of particulate matters P directly in the path of the gas stream within chamber 16 enables apparatus 10 to deliver particulate matters P of a wide range of sizes, and to mix and deliver a wide range of particulate matter types. The direct blow through mixing in chamber 16, permits operation at very low pressures, thereby increasing the range of operational pressures which may be selected.

Apparatus 10 contains no moving parts and is preferably made of disposable plastic, so that particulate matter P and apparatus 10 can be sterilized at the factory, and apparatus 10 replaced rather than re-filled and re-used. Apparatus 10 is designed to withstand common sterilization techniques such as Autoclave, chemical treatments, and irradiation. Contemplated apparatus 10 construction materials may include but are not limited to plastic, stainless steel, Delrin™ and Teflon™. Apparatus 10 is light-weight, manufactured to be re-cyclable, and easy to use and replace without training or maintenance.

Figure 5:
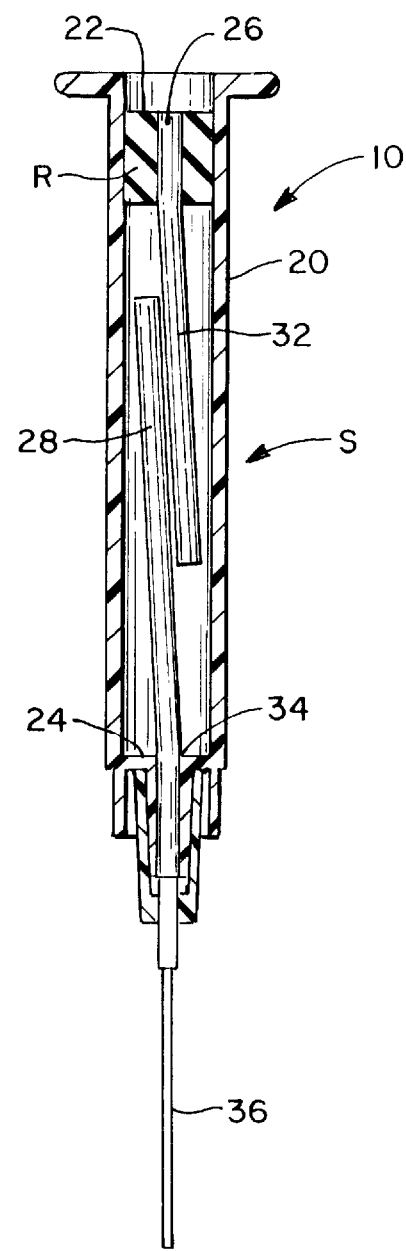
FIGS. 5 and 6 show alternative embodiments of the claimed apparatus, formed from a conventional industrial syringe.
Figure 6:
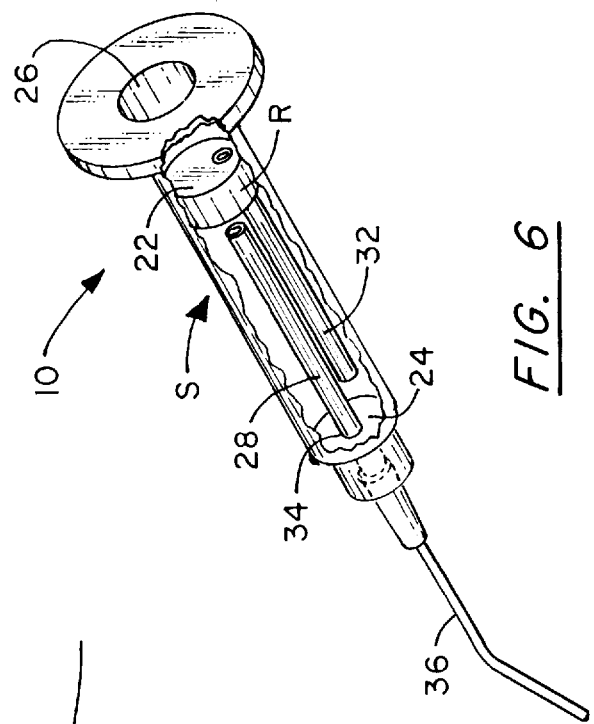
Figure 5A:
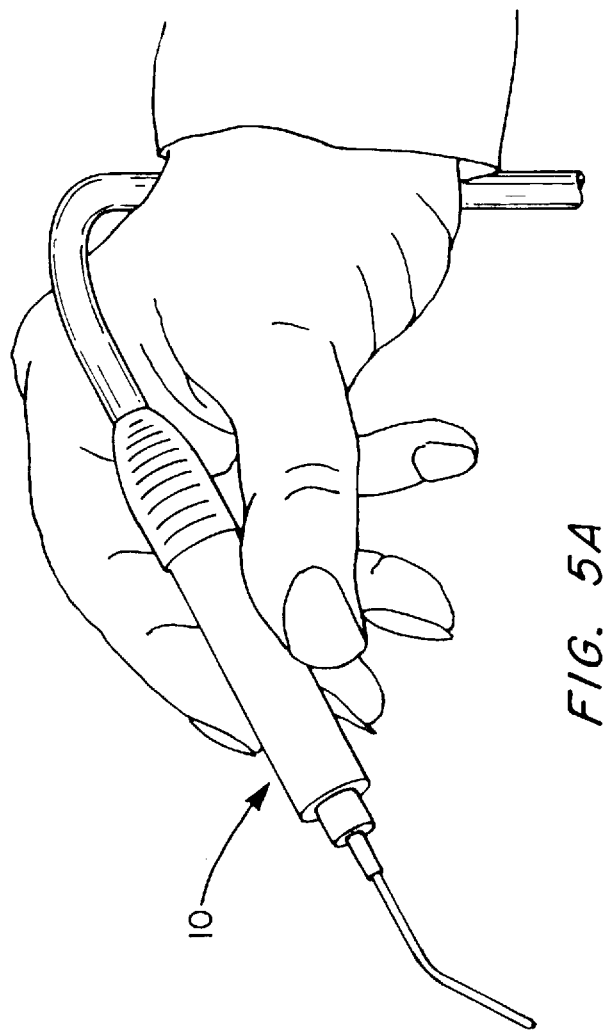
FIG. 5a is a perspective view of the apparatus of FIG. 5 in the hand of a user ready for operation.

Apparatus 10 can be constructed from an adapted disposable syringe S of a type which is extremely common in the health care industry. See FIGS. 5 and 6. Needle 36 is attached to a standard syringe needle with a dulled tip, and formed of either metal or plastic. Gas receiving port 26 is a hole bored into a standard rubber syringe stopper R separated from a standard syringe plunger. Mixture discharge port 34 is the existing discharge opening of the syringe S, while standard tubing can be used for gas delivery conduits 32 and 28.

Method

In practicing the invention, the following method may be used. A stream of gas A is delivered through gas receiving port 26 and gas delivery conduit 32 into chamber 16 from the gas air source (not shown). The gas stream A blows through the particulate matter P and causes the particulate matter P to mix with the gas stream in chamber 16. See FIG. 4. The air and particle mixture M enters and passes through discharge conduit 28, discharge port 34 and directing tube 36, and exists apparatus 10 to strike the target material T, without generating heat, vibration, appreciable noise levels, and having no moving parts.

In this manner there is provided a disposable apparatus powered by a compressed gas source for propelling particulate matter against a surface of a target material, more particularly against a surface of a dental patient's tooth, within the patient's mouth. The apparatus includes a mixing chamber having a chamber wall and a gas receiving port in the chamber wall in fluid communication with the compressed gas source and having a mixture discharge port in the chamber wall, a gas delivery conduit extending from the gas receiving port into the chamber, a mixture discharge conduit extending from the mixture discharge port into the chamber, and a quantity of particulate matter inside the chamber, wherein a steam of gas is delivered into the gas delivery conduit and into the mixing chamber from the gas source, the gas stream blows though the quantity of particulate matter and causes the particulate matter to mix with the gas stream in a mixing section on the chamber, forming a gas and particle mixture which enters and passes through the discharge conduit and the discharge port, and exits the apparatus to strike the surface of the patient's tooth.

The mixing chamber wall has a tubular side wall portion and two opposing end wall portions. The particulate matter does not completely fill said chamber. The chamber has a delivery conduit extending into the particulate matter. the chamber has a mixture discharge conduit extending into the mixing section of the chamber. A tubular particulate matter directing bendable tube is in fluid communication with the discharge port and extends outside and away from the chamber. The chamber may be formed of plastic, and may be color-coded to identify the particulate matter contained within the chamber.

Using this apparatus, particulate matter may be propelled against a surface of a target material by delivering a stream of gas into the gas delivery conduit and into the mixing chamber such that the gas stream blows through the particulate matter, thereby causing the particulate matter to mix with the gas stream, forming a gas/particle mixture, and discharging the gas/particulate mixture against a surface of the target.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim as my invention:

1. Handheld apparatus for propelling particulate matter against a surface of a patient's tooth, comprising:

a chamber having a sidewall, a first end wall at a one end of the chamber and a second end wall at an opposite end of the chamber;

a gas-receiving port in the first end wall;

a gas-delivery conduit disposed within the chamber and extending in fluid communication from the gas-receiving port towards the second end wall;

a discharge port in the second end wall;

a discharge conduit disposed within the chamber and extending in fluid communication from the discharge port towards the first end wall;

an elongate particle-directing tube disposed external the chamber, a proximal end of the particle-directing tube in fluid communication with the discharge port;

wherein:

the gas-delivery conduit abuts and is contiguous with both the sidewall and the first end wall of the chamber.

2. Handheld apparatus, according to claim 1, wherein:
the chamber is cylindrical.

3. Handheld apparatus, according to claim 1, wherein:
the gas-delivery conduit has a proximal end adjacent the gas-receiving port and a distal end spaced from the second end wall.

4. Handheld apparatus, according to claim 1, wherein:
the discharge conduit has a one end adjacent the discharge port and an opposite end spaced from the first end wall.

5. Handheld apparatus, according to claim 1, further comprising:
a quantity of particulate matter (P) disposed within the chamber and only partially filling the chamber.

6. Handheld apparatus, according to claim 5, further comprising:
markings on the chamber allowing visual observation of the quantity of particulate matter within the chamber.

7. Handheld apparatus, according to claim 1, further comprising at least one of:
an inlet cap for sealing the gas-receiving port; and
a tip cap for sealing a distal end of the particle-directing tube.

8. Handheld apparatus, according to claim 1, wherein:
the chamber is formed of a material selected from the group consisting of delrin (tm), teflon (tm), stainless steel and disposable plastic.

9. Handheld apparatus, according to claim 1, wherein:
wherein the sidewall is color-coded to indicate the type of particulate matter contained within the chamber.

10. Handheld apparatus for propelling particulate matter against a surface of a patient's tooth, comprising:
a chamber having a sidewall, a first end wall at a one end of the chamber and a second end wall at an opposite end of the chamber;
a gas-receiving port in the first end wall;
a gas-delivery conduit disposed within the chamber and extending in fluid communication from the gas-receiving port towards the second end wall;
a discharge port in the second end wall;
a discharge conduit disposed within the chamber and extending in fluid communication from the discharge port towards the first end wall;
an elongate particle-directing tube disposed external the chamber, a proximal end of the particle-directing tube in fluid communication with the discharge port;
wherein:
at least one of the first end wall and the second end wall abuts and is contiguous with the sidewall of the chamber.

11. Handheld apparatus, according to claim 10, wherein:
both of the first end wall and the second end wall abut and are contiguous with the sidewall of the chamber.

12. Handheld apparatus, according to claim 10, wherein:
the first end wall is made of rubber.

13. Handheld apparatus, according to claim 12, wherein:
the first end wall is a rubber syringe stopper; and
the gas-receiving port is a hole bored into the rubber syringe stopper.

14. Handheld apparatus, according to claim 10, wherein:
the sidewall and the second end wall are constructed from a disposable syringe.

15. Handheld apparatus, according to claim 10, further comprising:
a quantity of particulate matter (P) disposed within the chamber and only partially filling the chamber.

16. Handheld apparatus, according to claim 15, further comprising:
markings on the chamber allowing visual observation of the quantity of particulate matter within the chamber.

17. Handheld apparatus, according to claim 10, further comprising at least one of:
an inlet cap for sealing the gas-receiving port; and
a tip cap for sealing a distal end of the particle-directing tube.

18. Handheld apparatus, according to claim 10, wherein:
the chamber is formed of a material selected from the group consisting of delrin (tm), teflon (tm), stainless steel and disposable plastic.

19. Handheld apparatus, according to claim 10, wherein:
wherein the sidewall is color-coded to indicate the type of particulate matter contained within the chamber.

20. Handheld apparatus for propelling particulate matter against a surface of a patient's tooth, comprising:
a chamber having a sidewall, an opening at one end of the chamber, and an end wall at an opposite end of the chamber;
a rubber stopper disposed within the chamber at the one end of the chamber and having a gas-receiving port extending therethrough;
a gas-delivery conduit disposed within the chamber and extending in fluid communication from the gas-receiving port towards the second end wall;
a discharge port in the second end wall;
a discharge conduit disposed within the chamber and extending in fluid communication from the discharge port towards the rubber stopper; and
an elongate particle-directing tube disposed external the chamber, a proximal end of the particle-directing tube in fluid communication with the discharge port.

21. Handheld apparatus, according to claim 20, wherein:
turbulent mixing occurs in a portion of the chamber which is adjacent the first end wall.

22. Handheld apparatus, according to claim 20, further comprising:
a quantity of particulate matter (P) disposed within the chamber and only partially filling the chamber.

23. Handheld apparatus, according to claim 22, further comprising:
markings on the chamber allowing visual observation of the quantity of particulate matter within the chamber.

24. Handheld apparatus, according to claim 20, further comprising at least one of:
an inlet cap for sealing the gas-receiving port; and
a tip cap for sealing a distal end of the particle-directing tube.

25. Handheld apparatus, according to claim 20, wherein:
the chamber is formed of a material selected from the group consisting of delrin (tm), teflon (tm), stainless steel and disposable plastic.

26. Handheld apparatus, according to claim 20, wherein:
the sidewall is color-coded to indicate the type of particulate matter contained within the chamber.

27. Handheld apparatus, according to claim 10, wherein:
the particle-directing tube is bendable.

28. Handheld apparatus, according to claim 10, wherein:
the particle-directing tube is made of a material comprising metal and plastic.

29. Handheld apparatus, according to claim 10, wherein:
the particle-directing tube is of sufficient length to reach all surfaces of all teeth within a patient's mouth.

30. Handheld apparatus, according to claim 10, wherein:
the chamber has an axis;
a proximal portion of the particle-directing tube extends axially from the second end wall;
a distal portion of the particle-directing tube extends at an angle to the axis.

* * * * *

(12) EX PARTE REEXAMINATION CERTIFICATE (5312th)
United States Patent
Hertz

(10) Number: US 5,839,946 C1
(45) Certificate Issued: Mar. 28, 2006

(54) HANDHELD APPARATUS FOR PROPELLING PARTICULATE MATTER AGAINST A SURFACE OF A PATIENT'S TOOTH, AND METHOD

(75) Inventor: Reuben Hertz, Ft. Lauderdale, FL (US)

(73) Assignee: Barry B. Groman, Margate, FL (US)

Reexamination Request:
No. 90/006,225, Feb. 21, 2002

Reexamination Certificate for:
Patent No.: 5,839,946
Issued: Nov. 24, 1998
Appl. No.: 08/517,379
Filed: Aug. 21, 1995

(51) Int. Cl.
*B24C 5/04* (2006.01)
*B24C 7/00* (2006.01)

(52) U.S. Cl. .............. 451/90; 451/38; 451/99; 451/102

(58) Field of Classification Search ............. 451/90, 451/99, 102, 38, 89; 433/116, 125, 88; 222/630, 222/195
See application file for complete search history.

(56) References Cited

U.S. PATENT DOCUMENTS

| | | | | |
|---|---|---|---|---|
| 3,740,041 A | * | 6/1973 | Jones | 261/64.1 |
| 3,815,786 A | * | 6/1974 | McCallum | 222/642 |
| 4,990,140 A | * | 2/1991 | Black | 604/192 |
| 4,993,941 A | * | 2/1991 | Maita et al. | 433/80 |
| 5,150,822 A | * | 9/1992 | Eitner et al. | 222/145.1 |
| 5,199,229 A | * | 4/1993 | Herold et al. | 451/102 |
| 5,270,219 A | * | 12/1993 | DeCastro et al. | 436/180 |

\* cited by examiner

*Primary Examiner*—George Nguyen

(57) ABSTRACT

A disposable apparatus for propelling particulate matter against a surface of a target material includes, a mixing chamber having a chamber wall and a gas receiving port in the chamber wall in fluid communication with the compressed gas source and having a mixture discharge port in the chamber wall, a gas delivery conduit extending from the gas receiving port into the chamber, a mixture discharge conduit extending from the mixture discharge port into the chamber, and a quantity of particulate matter inside the chamber. A method is provided for propelling particulate matter against a surface of a target material using the above-described apparatus, including the steps of delivering a stream of gas into the air delivery conduit and into the mixing chamber from the gas source, so that the gas stream blows through the quantity of particulate matter, causing the particulate matter to mix with the gas stream, forming a gas and particle mixture, and discharging the mixture through the discharge conduit and the discharge port to strike the surface of the target material.

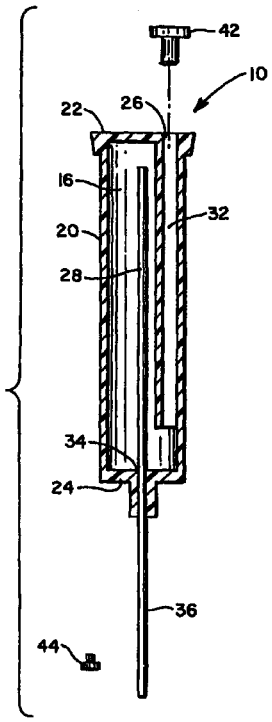

US 5,839,946 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 7, 17 and 24 are cancelled.

Claims 1, 8, 10, 18, 20, 25, 27, and 28 are determined to be patentable as amended.

Claims 2–6, 9, 11–16, 19, 21–23, 26, 29 and 30, dependent on an amended claim, are determined to be patentable.

New claims 31–49 are added and determined to be patentable.

1. Handheld apparatus for propelling particulate matter against a surface of a patient's tooth, comprising:
   a chamber having a sidewall, a first end wall at a one end of the chamber and a second end wall at an opposite end of the chamber;
   a gas-receiving port in the first end wall;
   a gas-delivery conduit disposed within the chamber and extending in fluid communication from the gas-receiving port towards the second end wall;
   a discharge port in the second end wall;
   a discharge conduit disposed within the chamber and extending in fluid communication from the discharge port towards the first end wall;
   an elongate particle-directing tube disposed external the chamber, a proximal end of the particle-directing tube in fluid communication with the discharge port;
   *an inlet cap for sealing the gas-receiving port; and*
   *a tip cap for sealing a distal end of the particle-directing tube*
   wherein:
   the gas-delivery conduit abuts and is contiguous with both the sidewall and the first end wall of the chamber.

8. Handheld apparatus, according to claim 1, wherein:
   the chamber is formed of a material selected from [the] *a* group *of materials* consisting of delrin (tm), teflon (tm), stainless steel and disposable plastic.

10. Handheld apparatus for propelling particulate matter against a surface of a patient's tooth, comprising:
    a chamber having a sidewall, a first end wall at a one end of the chamber and a second end wall at an opposite end of the chamber, *said chamber is used for containing said loose particulate matter*;
    a gas-receiving port in the first end wall;
    a gas-delivery conduit disposed within the chamber and extending in fluid communication from the gas-receiving port towards the second end wall, *wherein the particulate matter is mixed with the gas in the chamber used for storing said loose particulate matter*;
    a discharge port in the second end wall;
    a discharge conduit disposed within the chamber and extending in fluid communication from the discharge port towards the first end wall;
    an elongate particle-directing tube disposed external the chamber, a proximal end of the particle-directing tube in fluid communication with the discharge port; *and*
    *an inlet cap for sealing the gas-receiving port; and*
    *a tip cap for sealing a distal end of the particle-directing tube*
    wherein:
    at least one of the first end wall and the second end wall abuts and is contiguous with the sidewall of the chamber.

18. Handheld apparatus, according to claim 10, wherein:
    the chamber is formed of a material selected from [the] *a* group *of materials* consisting of delrin (tm), teflon (tm), stainless steel and disposable plastic.

20. Handheld apparatus for propelling particulate matter against a surface of a patient's tooth, comprising:
    a chamber having a sidewall, an opening at one end of the chamber, and an end wall at an opposite end of the chamber;
    a rubber stopper disposed within the chamber at the one end of the chamber and having a gas-receiving port extending therethrough;
    a gas-delivery conduit disposed within the chamber and extending in fluid communication from the gas-receiving port towards the second end wall;
    a discharge port in the second end wall;
    a discharge conduit disposed within the chamber and extending in fluid communication from the discharge port towards the rubber stopper; [and]
    an elongate particle-directing tube disposed external the chamber, a proximal end of the particle-directing tube in fluid communication with the discharge port, *and*
    *an inlet cap for sealing the gas-receiving port; and*
    *a tip cap for sealing a distal end of the particle-directing tube.*

25. Handheld apparatus, according to claim 20, wherein:
    the chamber is formed of a material selected from [the] *a* group *of materials* consisting of delrin (tm), teflon (tm), stainless steel and disposable plastic.

27. Handheld apparatus, according to claim 10, wherein:
    the particle-directing tube is *manually* bendable *making the discharge tube omni-directional*.

28. Handheld apparatus, according to claim 10, wherein:
    the particle-directing tube is made of a material [comprising] *selected from a group of materials consisting of* metal and plastic.

*31. A handheld apparatus for propelling particulate matter against a surface of a patient's tooth, comprising:*
    *a chamber being configured to be held in a hand comprising a sidewall, a first end wall at a one end of the chamber and a second end wall at an opposite end of the chamber,*
    *the chamber being a reservoir for storing particulate matter therein, and further being a mixing chamber for mixing the particulate matter stored therein with a gas supplied thereto;*
    *a gas-receiving port in the first end wall;*
    *a gas-delivery conduit disposed within the chamber and extending in fluid communication from the gas-receiving port towards the second end wall, the gas-delivery conduit abutting and being contiguous with both the sidewall and the first end wall of the chamber;* a discharge port in the second end wall;

a discharge conduit disposed within the chamber and extending in fluid communication from the discharge port towards the first end wall;

the gas delivery conduit comprising an gas entrance end coupled to the gas receiving port and a gas exit end located within said mixing chamber, the discharge conduit comprising an particle entrance end located within said mixing chamber and a discharge exit end coupled to said discharge port, wherein said gas exit end of gas delivery conduit is located closer to said discharge port compared to particle entrance end of said discharge conduit, wherein during normal operation the only way gas entering the mixing chamber via the gas delivery conduit can exit the mixing chamber is by passing through the particle entrance end of the discharge conduit, and an elongate particle-directing tube disposed external the chamber, a proximal end of the particle-directing tube in fluid communication with the discharge port.

32. The handheld apparatus, according to claim 31, wherein:

the handheld chamber is cylindrical.

33. The handheld apparatus, according to claim 31, wherein:

the gas-delivery conduit has a proximal end adjacent the gas-receiving port and a distal end spaced from the second end wall.

34. The handheld apparatus, according to claim 31, wherein:

the discharge conduit has a one end adjacent the discharge port and an opposite end spaced from the first end wall.

35. The handheld apparatus, according to claim 31, further comprising:

a quantity of particulate matter (P) disposed within the chamber and only partially filling the handheld chamber.

36. The handheld apparatus, according to claim 31, further comprising at least one of:

an inlet cap for sealing the gas-receiving port; and a tip cap for sealing a distal end of the particle-directing tube.

37. A handheld apparatus, comprising:

a chamber being configured to be held in a hand comprising a sidewall, a first end wall at a one end of the chamber and a second end wall at an opposite end of the chamber, at least one of the first end wall and the second end wall abutting and being contiguous with the sidewall of the chamber, the chamber being a reservoir for storing loose particulate matter therein, and further being a mixing chamber for mixing the particulate matter stored therein with a gas supplied thereto;

a gas-receiving port in the first end wall;

a gas-delivery conduit disposed within the chamber and extending in fluid communication from the gas-receiving port towards the second end wall, wherein the particulate matter is mixed with the gas in the chamber used for storing said loose particulate matter;

a discharge port in the second end wall;

a discharge conduit disposed within the chamber and extending in fluid communication from the discharge port towards the first end wall;

the gas delivery conduit comprising an gas entrance end coupled to the gas receiving port and a gas exit end located within said mixing chamber, the discharge conduit comprising an particle entrance end located within said mixing chamber and a discharge exit end coupled to said discharge port, wherein said gas exit end of gas delivery conduit is located closer to said discharge port compared to particle entrance end of said discharge conduit, wherein during normal operation the only way gas entering the mixing chamber via the gas delivery conduit can exit the mixing chamber is by passing through the particle entrance end of the discharge conduit, and an elongate particle-directing tube disposed external the chamber, a proximal end of the particle-directing tube in fluid communication with the discharge port.

38. The handheld apparatus, according to claim 37, wherein:

both of the first end wall and the second end wall abut and are contiguous with the sidewall of the chamber.

39. The handheld apparatus, according to claim 37, wherein:

the first end wall is made of rubber.

40. The handheld apparatus, according to claim 39, wherein:

the first end wall is a rubber syringe stopper; and the gas-receiving port is a hole bored into the rubber syringe stopper.

41. The handheld apparatus, according to claim 37, wherein:

the sidewall and the second end wall are constructed from a disposable syringe.

42. The handheld apparatus, according to claim 37, further comprising:

a quantity of particulate matter (P) disposed within the chamber and only partially filling the handheld chamber.

43. The handheld apparatus, according to claim 37, further comprising at least one of:

an inlet cap for sealing the gas-receiving port; and a tip cap for sealing a distal end of the particle-directing tube.

44. The handheld apparatus, according to claim 37, wherein:

the particle-directing tube is manually bendable making the discharge tube omni-directional in use.

45. The handheld apparatus, according to claim 37, wherein:

the particle-directing tube is of sufficient length to reach all surfaces of all teeth within a patient's mouth.

46. A handheld apparatus for propelling particulate matter against a surface of a patient's tooth, comprising:

a chamber having a sidewall, an opening at one end of the chamber, and an end wall at an opposite end of the chamber;

a rubber stopper disposed and fixed within the chamber at the one end of the chamber and having a gas-receiving conduit extending into the chamber;

a gas-delivery conduit disposed within the chamber and extending in fluid comunication from the gas-receiving port towards the second end wall;

a discharge port in the second end wall;

a discharge conduit disposed within the chamber and extending in fluid communication from the discharge port towards the rubber stopper;

wherein discharge the gas delivery conduit comprising an gas entrance end coupled to the gas receiving port and a gas exit end located within said mixing chamber, the discharge conduit comprising an particle entrance end located within said mixing chamber and a discharge exit end coupled to said discharge port, wherein said gas exit end of gas delivery conduit is located closer to said discharge port compared to particle entrance end of said discharge conduit, wherein during normal operation the only way gas entering the mixing chamber via the gas delivery conduit can exit the mixing chamber is by passing through the particle entrance end of the discharge conduit, and an elongate particle-directing tube disposed external the chamber, a proximal end of the particle-directing tube in fluid communication with the discharge port.

47. The handheld apparatus, according to claim 46, further comprising:

a quantity of particulate matter disposed within the chamber and only partially filling the chamber.

48. The handheld apparatus, according to claim 46, wherein the elongate particle-directing tube is manually bendable thereby providing an omni-directional discharge tube at the time of use.

49. The handheld apparatus, according to claim 46, further comprising at least one of:

an inlet cap for sealing the gas-receiving port; and a tip cap for sealing a distal end of the particle-directing tube.

* * * * *